(12) United States Patent
Lyon

(10) Patent No.: US 9,920,402 B2
(45) Date of Patent: Mar. 20, 2018

(54) MAGNESIUM ALLOYS CONTAINING HEAVY RARE EARTHS

(75) Inventor: Paul Lyon, Bolton (GB)

(73) Assignee: Magnesium Elektron Limited, Salford (GB)

( * ) Notice: Subject to any disclaimer, the term of this patent is extended or adjusted under 35 U.S.C. 154(b) by 0 days.

(21) Appl. No.: 13/582,877

(22) PCT Filed: Mar. 23, 2011

(86) PCT No.: PCT/GB2011/050577
§ 371 (c)(1),
(2), (4) Date: Nov. 7, 2012

(87) PCT Pub. No.: WO2011/117628
PCT Pub. Date: Sep. 29, 2011

(65) Prior Publication Data
US 2013/0195714 A1    Aug. 1, 2013

(30) Foreign Application Priority Data

Mar. 25, 2010 (GB) .................................. 1005031.8

(51) Int. Cl.
*C22C 23/06* (2006.01)
*C22C 23/00* (2006.01)
(Continued)

(52) U.S. Cl.
CPC ............ *C22C 23/06* (2013.01); *A61L 27/047* (2013.01); *A61L 31/022* (2013.01); *C22C 23/00* (2013.01)

(58) Field of Classification Search
CPC ..... A61L 27/047; A61L 31/022; C22C 23/00; C22C 23/06
(Continued)

(56) References Cited

U.S. PATENT DOCUMENTS

2004/0241036 A1* 12/2004 Meyer-Lindenberg ............................ A61L 27/047
420/405
2006/0228249 A1* 10/2006 Lyon ......................... C22F 1/06
420/406

(Continued)

FOREIGN PATENT DOCUMENTS

| CN | 101078080 A | 11/2007 |
|---|---|---|
| CN | 101130841 A | 2/2008 |

(Continued)

OTHER PUBLICATIONS

Neubert, V., et al., "Thermal stability and corrosion behaviour of Mg-Y-Nd and Mg-Tb-Nd Alloys", Materials Science and Engineering A: Structural Materials: Properties, Microstructure & Processing, Lausanne, CH, vol. 462, No. 1-2, May 1, 2007, 5 pages.

(Continued)

*Primary Examiner* — Jessee Roe
*Assistant Examiner* — Alexander Polyansky
(74) *Attorney, Agent, or Firm* — Winstead PC

(57) ABSTRACT

Magnesium alloys which possess good processability and/or ductility while retaining good resistance to corrosion and/or degradation comprising Y: 0-10% by weight, Nd: 0-5% by weight, wherein the total of Y+Nd is at least 0.05% by weight, one or more heavy rare earths selected from Ho, Lu, Tm and Tb in a total amount of above 0.5% and no more than 5.5% by weight, Gd: 0-3.0% by weight, and Sm: 0-0.2% by weight. The alloy optionally includes one or more of: Dy: 0-8% by weight; Zr: 0-1.2% by weight; Al: 0-7.5% by weight; Zn and/or Mn: 0-2% by weight in total; Sc: 0-15% by weight; In: 0-15% by weight; Ca: 0-3% by weight; Er up to 5.5% by weight, provided that the total of Er, Ho, Lu, Tm and Tb is no more than 5.5% by weight; and one or more rare earths and heavy rare earths other than Y, Nd, Ho, Lu, Tm, Tb, Dy, Gd and Er in a total amount of up to 0.5%

(Continued)

by weight; the balance being magnesium and incidental impurities up to a total of 0.3% by weight.

23 Claims, 2 Drawing Sheets

(51) Int. Cl.
 *A61L 27/04* (2006.01)
 *A61L 31/02* (2006.01)
(58) Field of Classification Search
 USPC .................................... 420/406; 623/11.11
 See application file for complete search history.

(56) References Cited

U.S. PATENT DOCUMENTS

| 2007/0227629 | A1* | 10/2007 | Gerold et al. | 148/420 |
| 2010/0082092 | A1* | 4/2010 | Gerold | 623/1.15 |
| 2011/0229365 | A1* | 9/2011 | Lyon et al. | 420/406 |
| 2011/0313527 | A1* | 12/2011 | Witte et al. | 623/11.11 |
| 2013/0060326 | A1 | 3/2013 | Gerold | |

FOREIGN PATENT DOCUMENTS

| EP | 141739 A2 | 5/1985 | |
| EP | 1842507 A1 | 10/2007 | |
| EP | 2 169 090 A1 | 3/2010 | |
| JP | 09104955 A * | 4/1997 | C22F 1/06 |
| WO | WO 2010017959 * | 2/2010 | A61L 27/00 |
| WO | WO-2010/038016 A | 4/2010 | |

OTHER PUBLICATIONS

González, J.J., "International Search Report" for PCT/GB2011/050577, dated Aug. 23, 2011, 3 pages.
Atrens, Andrej et al., "Overview of Stress Corrosion Cracking of Magnesium Alloys", 8th International conference on Magnesium Alloys—DGM, 2009, 9 pages.
English translation of Examiner-cited JP 09-104955 to Okita.

* cited by examiner

MAGNESIUM ALLOYS CONTAINING HEAVY RARE EARTHS

TECHNICAL FIELD

The present invention relates to magnesium alloys containing heavy rare earths which possess good processability and/or ductility, particularly when wrought, whilst retaining good resistance to corrosion and/or degradation, and are intended to be suitable for fabrication into medical implants, for example by extrusion.

BACKGROUND OF THE INVENTION

In our earlier filed International Patent application No. PCT/GB2009/002325 magnesium alloys are described which have a content of Erbium of up to 5.5% by weight and which demonstrate improvements in processability and/or ductility over known magnesium alloys such as those commercially known as Magnesium Elektron WE43 and WE54. These improved alloys also have equally good corrosion resistance of those known alloys when assessed using a standard salt fog test. Specifically for wrought applications the described alloys consist of:—
   Y: 2.0-6.0% by weight
   Nd: 0.05-4.0% by weight
   Gd: 0-5.5% by weight
   Dy: 0-5.5% by weight
   Er: 0-5.5% by weight
   Zr: 0.05-1.0% by weight
   Zn+Mn: <0.11% by weight,
   Yb: 0-0.02% by weight
   Sm: 0-0.04% by weight,
   optionally rare earths and heavy rare earths other than Y, Nd, Gd, Dy, Er, Yb and Sm in a total amount of up to 0.5% by weight, and
the balance being magnesium and incidental impurities up to a total of 0.3% by weight, %, wherein
the total content of Gd, Dy and Er is in the range of 0.3-12% by weight, and
wherein the alloy exhibits a corrosion rate as measured according to ASTM B117 of less than 30 Mpy.
   For casting applications the described alloys consist of:—
   Y: 2.0-6.0% by weight
   Nd: 0.05-4.0% by weight
   Gd: 0-5.5% by weight
   Dy: 0-5.5% by weight
   Er: 0-5.5% by weight
   Zr: 0.05-1.0% by weight
   Zn+Mn: <0.11% by weight,
   optionally rare earths and heavy rare earths other than Y, Nd, Gd, Dy and Er in a total amount of up to 20% by weight, and
the balance being magnesium and incidental impurities up to a total of 0.3% by weight, wherein
   the total content of Gd, Dy and Er is in the range of 0.3-12% by weight, and wherein
   when the alloy is in the T4 or T6 condition the area percentage of any precipitated particles having an average particle size of between 1 and 15 μm is less than 3%.

Our earlier application refers to the previous belief held by experts such as King that the behaviour of the heavy rare earths as alloying constituents was essentially the same and that therefore in magnesium alloys such as WE43 heavy rare earths such as Erbium and Ytterbium were interchangeable. Investigations revealed, however, that such prior belief was not well founded, as revealed by the solid solubility values of individual heavy rare earths in magnesium as set out in Table 2 of PCT/GB2009/002325.

Furthermore in our earlier application Gd, Dy and Er were considered to be essentially equivalent, with each being present in an amount of up to 5.5% by weight. However, the solid solubility data in Table 2 of PCT/GB2009/002325 suggested that the use of Er should be more advantageous than the use of Gd and Dy, and further work has now confirmed this.

Further work has also now established that at the temperatures that magnesium alloys are wrought Terbium is almost as soluble in magnesium as Dysprosium, Holmium possesses a solid solubility in magnesium greater than Dysprosium and is almost as soluble as Erbium, whilst Thulium, and especially Lutetium, possess solid solubilities superior to Erbium. Thus in the present invention one or more of the heavy rare earths Ho, Lu, Tm and Tb can replace the Er used in the alloys of PCT/GB2009/002325 either partly or totally.

The solid solubility limits of the heavy rare earths and selected other rare earths in pure magnesium at various temperatures, including room temperature "RT", is set out in Table 1. It will be appreciated, however, that for magnesium alloys containing other alloying elements these limits will vary.

TABLE 1

| Atomic number | Element | RT | 300° C. | 400° C. | 500° C. |
|---|---|---|---|---|---|
| 71 | Lu | 10-12 | 19.5 | 25 | 35 |
| 70 | Yb | ca. 0 | 0.5 | 1.5 | 3.3 |
| 69 | Tm | 10-12 | 17.6 | 21.7 | 27.5 |
| 68 | Er | 10-12 | 18.5 | 23 | 28.3 |
| 67 | Ho | 8-10 | 15.4 | 19.4 | 24.2 |
| 66 | Dy | ca. 5 | 14 | 17.8 | 22.5 |
| 65 | Tb | 1-2 | 12.2 | 16.7 | 21.0 |
| 64 | Gd | ca. 0 | 3.8 | 11.5 | 19.2 |
| 63 | Eu | 0 | 0 | 0 | 0 |
| 62 | Sm | ca. 0 | 0.8 | 1.8 | 4.3 |
| 61 | Pm | — | — | — | — |
| 60 | Nd | ca. 0 | 0.16 | 0.7 | 2.2 |
| 59 | Pr | ca. 0 | 0.05 | 0.2 | 0.6 |
| 58 | Ce | ca. 0 | 0.06 | 0.08 | 0.26 |
| 57 | La | ca. 0 | 0.01 | 0.01 | 0.03 |
| 39 | Y | 1-2 | 4.2 | 6.5 | 10.0 |
| 21 | Sc | ca. 12 | 12.8 | 15.7 | 18.8 |

Although for wrought applications, particularly for structural applications, it was considered that rare earths and heavy rare earths other than Y, Nd, Gd, Dy, Er, Yb and Sm could be present in the total amount of up to 0.5% by weight, provided that the alloy exhibited a corrosion rate as measured according to ASTM B117 of less than 30 Mpy, it has been found that when preparing a magnesium of the type described for use as a medical implant, for example picking up the teaching of EP141739 and 1842507 which require the alloy to be wrought, particularly by extrusion, and must meet additional criteria for such medical use, the limits as set out in PCT/GB2009/002325 can and must be adjusted. For example previously it was considered that, because of the need to retain in the alloys of PCT/2009/002325 mechanical properties, particularly tensile strength, equal to or greater than WE43 type alloys, a greater than impurity amount of cerium and lanthanum could be present and no more than an impurities amount of scandium could be tolerated. However, since for medical uses such as bone-replacement implants, such high mechanical properties are of lesser importance than the behaviour of the alloy in a biological setting, for example its biodegradable characteristics, these prior believed limitation and tolerance concerning cerium, lanthanum and scandium are in fact for the present alloys reversed.

Similarly, whereas it had been thought that an alloy's corrosion behaviour in a standard salt fog test could be used as a guide to its behaviour in a corrosion test in simulated body fluid (SBF), this has been found for some alloys of the present invention not to be the case. Whilst for some their salt fog corrosion behaviour is similar to that of the some of the reference alloys, all of the alloys of the present invention have improved resistance to degradation in SBF when compared to that of the known alloys WE43 and WE54.

As explained in PCT/GB/2009/002325, it is also important for good ductility that the occurrence in the alloy of large particles or clusters of particles be controlled.

SUMMARY OF THE INVENTION

Accordingly, the present invention provides a magnesium alloy suitable for fabricating into a medical implant comprising:
Y: 0-10% by weight,
Nd: 0-5% by weight,
wherein the total of Y+Nd is at least 0.05% by weight,
one or more heavy rare earths selected from Ho, Lu, Tm and Tb in a total amount of above 0.5% and no more than 5.5% by weight,
wherein optionally the alloy includes one or more of:
Dy: 0-8% by weight,
Gd: 0-7% by weight,
Zr: 0-1.2% by weight,
Al: 0-7.5% by weight,
Zn and/or Mn: 0-2% by weight in total,
Sc: 0-15% by weight,
In: 0-15% by weight,
Ca: 0-3% by weight,
Er up to 5.5% by weight provided that the total of Er, Ho, Lu, Tm and Tb is no more than 5.5% by weight, and
one or more rare earths and heavy rare earths other than Y, Nd, Ho, Lu, Tm, Dy, Gd and Er in a total amount of up to 0.5% by weight,
the balance being magnesium and incidental impurities up to a total of 0.3% by weight.

As mentioned above, magnesium has many advantages for biomedical applications, for example biodegradable inserts like stents, screws/plates/reinforcement for bone repair and surgical suture materials/staples. For many applications however, the time for degradation (corrosion) and failure of the magnesium repair device is too soon and can develop too much gas evolution ($H_2$) during the corrosion process. Additionally failure of stressed magnesium devices can occur due to Environmentally Assisted Cracking (EAC). EAC also referred to as Stress Corrosion Cracking (SCC) or Corrosion Fatigue (CF) is a phenomenon which can result in catastrophic failure of a material. This failure often occurs below the Yield Strength (YS). The requirement for EAC to occur is three fold, namely mechanical loading, susceptible material, and a suitable environment.

ECSS (European Cooperation for Space Standardisation), quantifies the susceptibility of various metallic alloys by use of an industry recognised test, employing aqueous NaCl solution. ECSS-Q-70-36 report ranks the susceptibility of several Magnesium alloys, including Mg—Y—Nd-HRE-Zr alloy WE54. This reference classifies materials as high, moderate or low resistance to SCC. WE54 is classed as "low resistance to SCC" (ie poor performance). For biomedical applications, stresses are imposed on the materials and the in vivo environment (e.g. blood) is known to be most corrosive. As for the ECSS tests, SBF is widely used for in vitro testing and includes NaCl. Tests described in this patent application suggest that EAC performance of the Mg—Y—Nd-HRE-Zr alloy system can be improved by selective use of HRE additions. This offers a significant benefit for biomedical implants, where premature failure could have catastrophic results, for example Atrens (Overview of stress corrosion cracking of magnesium alloys—8th International conference on Magnesium alloys—DGM 2009), relates potential use of stents in heart surgery, whereby fracture due to SCC would probably be fatal. The consequence of premature failure may include re intervention, patient trauma, etc. The alloys used must still be formable and show sufficient strength.

The use of the inventive Mg alloy for manufacturing an implant causes an improvement in processability, an increase in corrosion resistance and biocompatibility compared to conventional magnesium alloys, especially WE alloys such as WE43 or WE54.

Unlike the alloy of PCT/GB2009/002325, it has been found that both Yttrium and Neodymium can be completely absent or present only as an incidental impurity, provided that in total Y+Nd is at least 0.05% by weight, preferably at least 0.1% by weight, in order to provide the alloy with sufficient strength or degradation performance. Freed of the constraints of the alloys of PCT/GB2009/002325 but whilst retaining sufficient durability for extrusion without cracking, Yttrium can be present up to 10% by weight, preferably at least 0.05% by weight, more preferably 0.05-5% by weight, and even more preferably 3.7-4.2% by weight. Similarly Nd can be present up to 5% by weight, preferably at least 0.05% by weight, more preferably 0.05-2.5% by weight, and even more preferably above 1.3% by weight. The reduction in coarse particles previously described as being beneficial to the alloys of PCT/GB2009/002325 is also useful for the alloys of the present invention because the presence of such coarse particles tends to reduce the alloy's formability and may affect its biodegradability.

The essential heavy rare earths Ho, Lu, Tm and Tb are present in a total amount greater than the 0.5% by weight and up to 5.5% by weight, with Er being optionally additionally present to replace some but not all of the Ho, Lu, Tm or Tb. In other words Er can be present in an amount of up to 5.5% by weight, provided that the total amount of Er, Ho, Lu, Tm and Tb is no more than 5.5% by weight. Preferably these heavy rare earths are present in an amount of up to 4% by weight, and more preferably up to 1% by weight, with the most preferred of these heavy rare earths for some medical implant applications being Lu or Tm, because of their high solid solubility in magnesium according to Table 1. Preferably Lu is present in an amount of at least 0.1% by weight. In some embodiments, the content of Ho in the Mg alloy is 1-4% by weight, preferably 1.5-3.5% by weight.

The total content of Ho, Lu, Tm, Tb, Er, Dy and Gd in the Mg alloy is preferably 0.2-9% by weight, more preferably 2-6% by weight, more preferably 3-5% by weight. In some alloys, a total content of Ho, Lu, Tm, Tb, Er, Dy and Gd in the Mg alloy of 0.3-4.0% by weight is preferred. The total content of Ho, Lu, Tm, Tb, Er, Nd, Dy and Gd in the Mg alloy is preferably 4-10% by weight, more preferably 5-9% by weight. In some alloys, a total content of Ho, Lu, Tm, Tb, Er, Nd, Dy and Gd in the Mg alloy of 1-5.5% by weight is preferred. Preferably, the total content of rare earths (excluding Y and Nd) other than Gd, Dy, Ho, Lu, Tm and Tb is less than 13% of the total weight of Gd, Dy, Ho, Lu and Tm. In some embodiments, individually each of Ho, Lu, Tm and Tb cannot be present in the Mg alloy an amount of greater than 4% by weight.

The content of Mg in the Mg alloy is preferably at least 85% by weight, more preferably at least 87% by weight. In some embodiments, the Mg content is at least 91% by weight.

The content of Gd in the Mg alloy is 0-7% by weight, preferably 0-5% by weight, more preferably 0-3.0% by weight, more preferably less than 2.5% by weight, and even more preferably 0-2% by weight. Gd can reduce the degradation of the alloy in SBF tests and improve its EAC behaviour. Levels of Gd approaching the solubility limit in a given alloy reduce ductility. For some alloys Gd content can be less than 1% by weight, preferably less than 0.5% by weight, whilst for others Gd can be avoided altogether.

The content of Dy in the Mg alloy is 0-8% by weight, preferably 0-4% by weight, more preferably 0-0.6% by weight. Dy behaves in a similar manner to Gd.

In addition, the content of Zr in the Mg alloy is 0-1.2% by weight, preferably at least 0.01% by weight, more preferably at least 0.05% by weight, and even more preferably 0.1-0.8% by weight. In some embodiments, the Zr content in the Mg alloy is less than 0.15% by weight. For magnesium-zirconium alloys, zirconium has a significant benefit of reducing the grain size of magnesium alloys, especially of the pre-extruded material, which improves the ductility of the alloy. Further, Zr removes contaminants from the melt.

The content of Zn and/or Mn in the Mg alloy is 0-2% by weight, preferably 0-0.5% by weight, more preferably less than 0.40% by weight and even more preferably less than 0.2% by weight. Both Zn and Mn can contribute to precipitation and can also affect general corrosion, but Zn is preferred to Mn. For some alloys Zn addition should be avoided altogether. For some alloys, it is preferred to avoid addition of Mn because it can reduce the grain-refining effect of Zr.

The content of Yb in the Mg alloy is preferably 0-0.02% by weight, preferably less than 0.01% by weight.

The content of Ti in the Mg alloy is preferably less than 0.1% by weight, more preferably less than 0.05% by weight and even more preferably less than 0.01% by weight. For some alloys, Ti addition should be avoided altogether.

The content of Si in the Mg alloy is preferably less than 0.1% by weight, more preferably less than 0.05% by weight and even more preferably less than 0.01% by weight. For some alloys, it is preferred to avoid addition of Si because it can reduce the grain-refining effect of Zr.

The content of Sm in the Mg alloy is preferably 0-0.2% by weight, more preferably 0-0.1% by weight, even more preferably 0-0.04% by weight, more preferably less than or equal to 0.02% by weight. These low levels of Sm are preferred because excessive Sm may lead to increased brittle particles. For some alloys Sm addition should be avoided altogether (ie Sm should not be intentionally added).

For the remaining alloying elements referred to in PCT/GB2009/002325 their essential ranges are generally expanded whilst their preferred ranges are in line with those described in the earlier application for the reasons given in PCT/GB2009/002325, such as particle size. These ranges are set out in the accompanying claims, although for some alloys Gd addition should be avoided altogether.

It has also been found that the presence of some alloying elements which are potentially useful in medical implant applications can additionally be present. These are specifically:—

Al: 0-7.5% by weight
Sc: 0-15% by weight
Ca: 0-3% by weight

The content of In in the Mg alloy is 0% by weight up to its solubility limit, which in the present alloys can be as high as about 15% by weight, and preferably no more than 5% by weight. In can have a benefit of improving corrosion performance in some alloys. For some alloys In addition should be avoided altogether.

The content of Sc in the Mg alloy is 0% by weight up to its solubility limit, which in the present alloys can be as high as about 15% by weight, and preferably no more than 7% by weight, more preferably no more than 5% by weight. Sc can have a positive effect on corrosion resistance. For some alloys Sc addition should be avoided altogether.

Al can be added to the Mg alloy in an amount for some alloys as high as 7.5% by weight, but generally should be added in an amount less than 6% by weight in order not to significantly adversely affect the alloy's strength, ductility or biodegradability behaviour. Preferably any Al addition should be no higher than 4%, more preferably less than 3% by weight, even more preferably less than 1% by weight and more preferably 0.2-0.8% by weight. In some embodiments, Al addition should be less than 0.05% by weight. For some alloys Al addition should be avoided altogether (ie Al should not be intentionally added).

The content of Ca in the Mg alloy is 0-3% by weight, preferably 0-1% by weight. Ca can have a significant benefit of reducing the grain size of magnesium alloys. For some alloys Ca addition should be avoided altogether.

The alloys of the present invention preferably exhibit a corrosion rate as measured according to ASTM B117 of less than 40 Mpy, more preferably less than 30 Mpy.

Preferably the area percentage of any precipitated particles formed during processing of the alloys of the present invention having an average particle size of between 1 and 20 μm is less than 5%. Preferably the said particles are rich in Nd, such that the particles have a percentage composition of Nd greater than the percentage composition of any other element in the particle.

Preferably, when the alloys of the present invention are in the T4 or T6 condition the area percentage of any precipitated particles having an average particle size of between 1 and 15 μm is less than 3%. More preferably, when the alloys of the present invention are in the T4 or T6 condition the area percentage of particles having an average size greater than 1 μm and less than 15 μm is less than 1.5%. Even more preferably, when the alloys of the present invention are in the T4 or T6 condition the area percentage of particles having an average size greater than 1 μm and less than 7 μm is less than 3%.

As with PCT/GB2009/002325 the total of incidental impurities should be limited to 0.3% by weight, with certain defined impurities having individual maximum impurity levels as recited in PCT/GB2009/002325.

DESCRIPTION OF THE DRAWINGS

The present disclosure is explained in greater detail in the following on the basis of exemplary embodiments and the associated drawings.

DETAILED DESCRIPTION OF THE INVENTION

Figure 1:
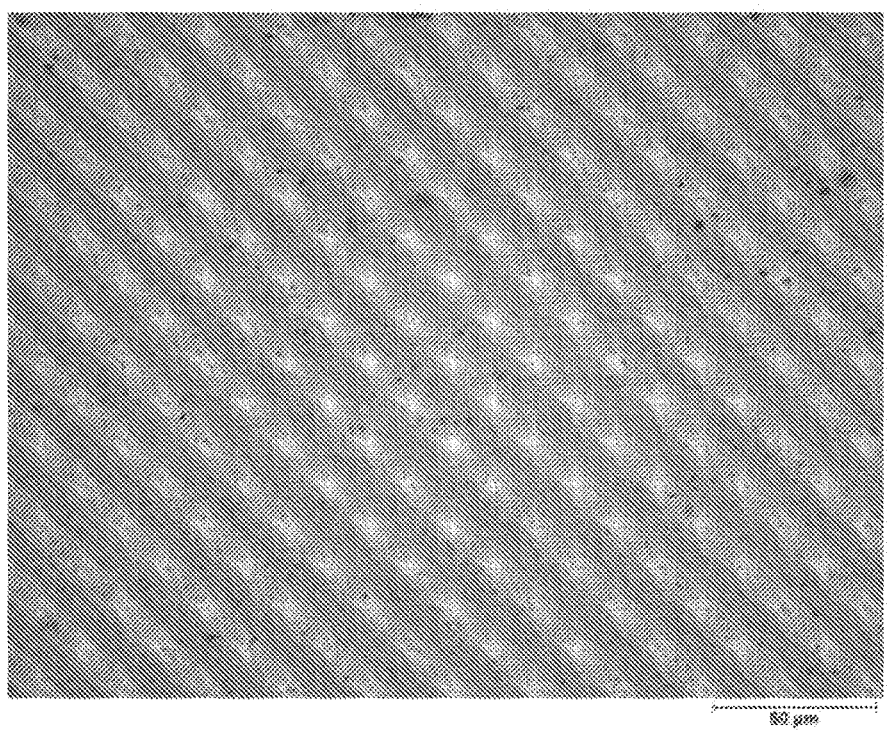
FIG. 1-3 show microstructures of the samples.

The preparation of test samples of the alloys of the present invention were prepared and tested and analysed in the same manner as described in PCT/GB2009/002325.

Several melts with different alloy compositions were melted cast, and extruded and subsequently subject to different investigation with the emphasis on the microstructure (grain size, size, fraction and composition of precipitates), the respective thermo-mechanical properties (tensile properties) and the corrosion behaviour with and without superimposed mechanical load. In addition bio compatibility tests were carried out. In general, melts were carried out according to the following casting technique:

High-purity starting materials (generally ≥99%) were melted in steel crucibles under a protective gas ($CO_2$/2% $SF_6$). The temperature was raised to 760° C. to 800° C. before the melt was homogenized by stirring. The melt was cast to form bars with a nominal diameter of 120 mm and a length of 300 mm. Next the bars were machined to a nominal diameter of 75 mm with a length of 150 mm to 250 mm and homogenized for 4-8 hours. Near to the melts' solidus temperature, homogenization was typically achieved at approximately 525° C.

The material was then heated to 350-500 C and extruded with the help of a hydraulic press. The resulting round rods had a diameter in the range of 6 mm to 16 mm, mostly 9.5-12.7 mm. For the following investigations, pieces from the start and end of an extrusion 30 cm long were usually removed.

Table 2 summarises the chemical compositions, corrosion rates and tensile properties of exemplary Mg alloys. MI0007, MI0034 and SF4619 are comparative examples of WE43 type alloys falling within AMS4427 chemical specification used as reference material. Each time, melts were produced to generate tensile data and for metallography.

Mechanical Properties and Metallurgical Description

To determine the mechanical properties, standardized tension tests of the bulk materials were performed and analyzed using several samples of a melt in each case. The 0.2% yield tensile strength (YTS), the ultimate tensile strength (UTS) and elongation at fracture (A) were determined as characteristic data. The yield strength YS of a material is defined as the stress at which material strain changes from elastic deformation to plastic deformation, causing it to deform permanently. The ultimate tensile strength UTS is defined as the maximum stress a material can withstand before break.

For the metallographic examination of the as extruded condition the materials were melted, cast, homogenized, cut to billets and extruded to bars. Then samples were cut, embedded in epoxy resin, ground, polished to a mirror like finish and etched according to standard metallographic techniques [G Petzow, Metallographisches, keramographisches and plastographisches Ätzen, Borntraeger 2006].

Discussion of Bulk Material Mechanical Properties

Table 2 summarises the chemical composition, mechanical (tensile test) and corrosion (salt fog in NaCl and immersion in SBF) properties of Mg alloys. As can be seen from the data of Table 2, the inventive changes in the composition of the alloys provide tensile properties which are similar to the reference in terms of strength and ductility.

Microstructure

Figure 2:
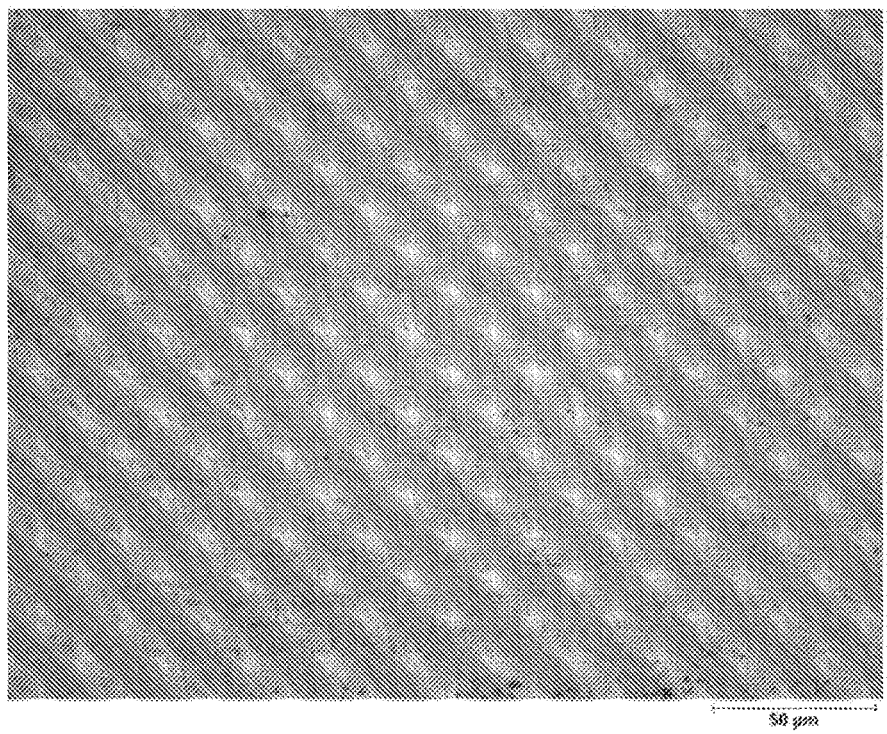
Figure 3:
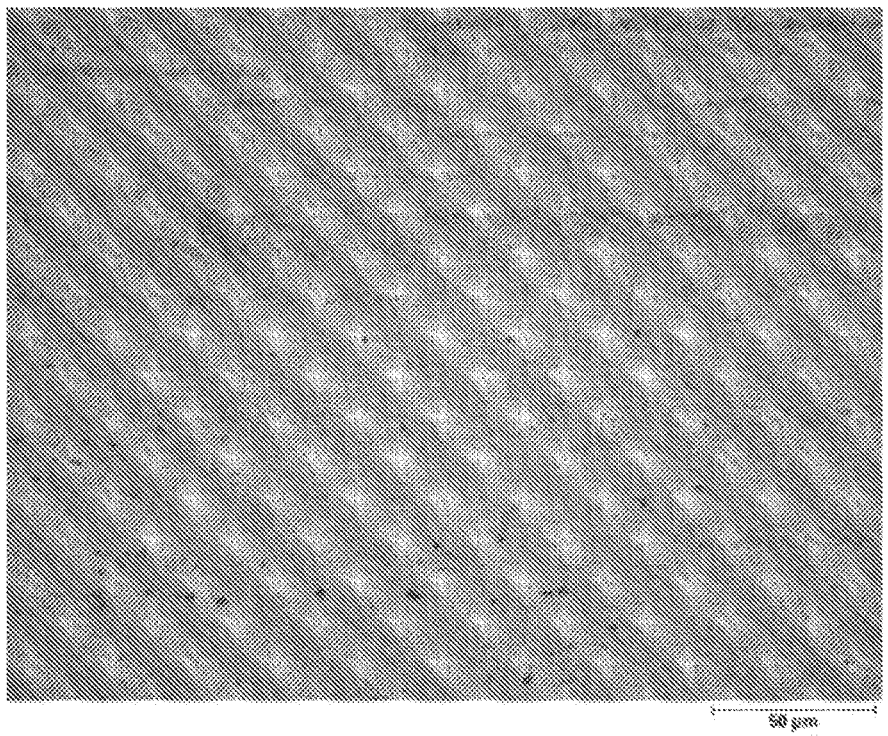

FIGS. 1 through 3 show microstructures of exemplary samples (FIG. 1: MI101/FIG. 2: MI102/FIG. 3: MI103) after extrusion. They provide an insight into the effect of alloy composition upon strength and ductility of some of the alloys examples. A microstructure which is free of large particles and clusters ("clean microstructure") can offer the advantage of improved ductility if the clusters/particles are brittle.

FIGS. 1 through 3 all show "clean microstructures" which are largely free of particles. In addition, FIG. 2 shows the effect of adding increased Nd to an alloy similar to that shown in FIG. 3. It would normally be expected that adding additional Nd, close to the solid solubility limit, would increase second phase retention, resulting in a microstructure which has more clusters and a lower ductility. However, it has surprisingly been found that the alloy in FIG. 2 has a similar microstructure to those in FIGS. 1 and 3. Without wishing to be bound to any theory, it is thought that this might be due to the inclusion of Ho in the alloy of FIG. 2, which may help to suppress second phase formation and thereby reduce the number and size of any particles.

Corrosion Behaviour

The corrosion behaviour of selected alloy systems was investigated in greater detail on the basis of three standardized tests. The results of these tests are summarized in Table 2.

TABLE 2

| Identity | Chemical Analysis (weight %) | | | | | | | | | | | | | | |
|---|---|---|---|---|---|---|---|---|---|---|---|---|---|---|---|
| | Y | Nd | Zr | Gd | Dy | Yb | Er | Sm | La | Ce | Pr | Ho | Lu | Al | Fe | TRE[1] |
| Reference alloys | | | | | | | | | | | | | | | | |
| MI0034 | 3.8 | 2.3 | 0.54 | 0.44 | 0.47 | 0 | 0.01 | 0.01 | 0.00 | — | | | | 0.01 | 0.002 | 0.93 |
| MI0007 | 4 | 2.2 | 0.57 | 0.46 | 0.46 | 0 | — | — | 0.00 | — | | | | 0.01 | 0.002 | 0.92 |
| SF4619 | 3.9 | 2.2 | 0.56 | 0.28 | 0.30 | 0.03 | 0.09 | 0.03 | 0.00 | 0.00 | | | | 0.002 | 0.002 | 0.73 |
| Example Alloys of Invention | | | | | | | | | | | | | | | | |
| MI101 | 4.2 | 2.6 | 0.59 | 0.1 | 0.52 | 0.00 | 0.02 | 0.02 | 0.00 | 0.01 | 0.00 | 3 | | 0.01 | 0.002 | 3.67 |
| MI102 | 3.80 | 3.35 | 0.62 | 0.06 | 0.55 | 0.00 | 1.64 | 0.02 | 0.00 | 0.01 | 0.00 | 2 | | 0.01 | 0.002 | 4.28 |
| MI103 | 3.80 | 2.30 | 0.79 | 0.11 | 0.48 | 0.00 | 1.72 | 0.02 | 0.00 | 0.01 | 0.00 | | 2 | 0.01 | 0.004 | 4.34 |
| Additional Example | | | | | | | | | | | | | | | | |
| MI0024 | 4 | 2.4 | 0.6 | 0 | 0 | 0.00 | 1.74 | 0.00 | 0.00 | 0.00 | 0.00 | | | 0.01 | 0.002 | 1.74 |
| MI0023 | 3.9 | 2.3 | 0.57 | 0.48 | 0.54 | 0.00 | 7.35 | 0.02 | 0.00 | 0.01 | 0.00 | | | 0.01 | 0.002 | 8.40 |

TABLE 2-continued

|  | Tensile Properties | | | Corrosion Properties | | |
| --- | --- | --- | --- | --- | --- | --- |
|  | 0.2% YS | UTS | Elong | NaCl | SBF | |
| Identity | MPa | MPa | % | mpy[2] | mpy | % of Reference |
| Reference alloys | | | | | | |
| MI0034 | 210 | 290 | 26 | 12 | 775 | 100 |
| MI0007 | 210 | 291 | 26 | 14 | 835 | NA |
| SF4619 | 209 | 298 | 19 | 56 | ND | NA |
| Example Alloys of Invention | | | | | | |
| MI101 | 206 | 298 | 26 | 11 | 90 | 40 |
| MI102 | 214 | 299 | 26 | 10 | 118 | 40 |
| MI103 | 204 | 288 | 25 | 25 | 255 | 85 |
| Additional Example | | | | | | |
| MI0024 | 217 | 294 | 23 | 15 | 477 | 92 |
| MI0023 | 276 | 348 | 14 | 18 | 206 | 40 |

[1]TRE here is the sum of Gd, Dy, Yb, Er, Sm, La, Ce, Pr, Ho, Lu

Salt Fog Test

First a standardized test to evaluate the industrial usability of the alloys was performed using a 5% NaCl-containing spray mist according to ASTM B117. The samples were exposed to the test conditions for the required number of days and then the corrosion product was removed by boiling in a 10% chromium trioxide solution. The weight loss of the samples was determined and expressed in mpy (mils penetration per year) as is customary in international practice.

Immersion in SBF

The corrosion resistance also depends on the corrosion medium. Therefore, an additional test method has been used to determine the corrosion behaviour under physiological conditions in view of the special use of the alloys.

For storage in SBF (simulated body fluid) with an ionic concentration of 142 mmol/L $Na^+$, 5 mmol/L $K^+$, 2.5 mmol/L $Ca^{2+}$, 1 mmol/l $Mg^{2+}$, 1 mmol/l $SO_4^{2-}$, 1 mmol/l $HPO_4^{2-}$, 109 mmol/l $Cl^-$ and 27 mmol/L $HCO_3^-$ cylindrical samples of the extruded material are completely immersed in the hot medium for 7 days at nominally 37° C. The corrosion product is then removed by boiling in a 10% chromium trioxide solution. As for the ASTM B117 test, the weight loss of the samples was determined and expressed in mpy.

An important factor to note is that the absolute value can vary with each batch test. This can make comparison of absolute values difficult. To resolve this, a standard (known reference WE43-type alloy, for example MI0034 type alloy) is tested with each batch of alloys tested. The reference is then used as a basis to compare any improvements. Reference is given the value 100% and values less than this show an improvement (less degradation).

Results of Salt Fog Test

All three of the inventive alloys that were tested showed good performance in the salt fog test. In addition, it was surprisingly found that the alloys comprising Ho, MI101 and MI102, were particularly good, with values of 11 Mpy and 10 Mpy respectively.

Results of Immersion in SBF

Tests in immersed SBF, of the alloys of the invention, surprisingly illustrate a significant improvement in performance when compared to the reference WE43 type alloy. This significant improvement in SBF is not revealed by the results of the salt fog test. Within this improvement, it was again surprisingly found that the alloys comprising Ho, MI101 and MI102, were particularly good, both having values that are 40% of the reference alloy.

Referring to the additional examples, alloy MI0024 shows that the inclusion of 1.74% by weight Er gives a slight improvement in corrosion performance in SBF (92%). However, this can be contrasted with alloy of the invention MI102 which also includes 2% Ho (~4% by weight total HRE) and which shows a significant improvement in corrosion performance in SBF (40%).

To illustrate that this improvement is not simply an effect of doubling the HRE content, additional example alloy MI0023 shows that it is necessary to include 7.5% Er (~8.5% by weight HRE) in order to achieve the same 40% SBF value as that achieved by alloy MI102.

Although described with particular reference to medical implants the alloys of the present invention have a variety of other uses and can be cast and/or heat treated and/or wrought and/or used as a base alloy for a metal matrix composite and/or rapidly solidified to produce an amorphous form, such as a powder or wire, and/or forged or extruded in any way.

The invention claimed is:

1. A medical implant comprising a magnesium alloy composition, the composition consisting of:
    Y in an amount of ≤0.3% by weight,
    Nd in an amount of 0.05-5% by weight,
    one or more heavy rare earths selected from Ho, Lu, Tm and Tb of above 0.5% by weight each and no more than 5.5% by weight in total,
    Zr in an amount of 0.1-0.8% by weight,
    Gd in an amount of 0-7% by weight,
    one or more of Zn, Mn, Yb, Sm, Al, Fe, Dy, Er, La, Si and Magnesium.

2. The alloy as claimed in claim 1 wherein Zn and/or Mn are present in an amount of up to 2% by weight in total.

3. The alloy as claimed in claim 1 wherein Yb is present in an amount of up to 0.02% by weight.

4. The alloy as claimed in claim 3 wherein the Yb content is less than 0.01% by weight.

5. The alloy as claimed in claim 1 wherein Sm is present in an amount of up to 0.04% by weight.

6. The alloy as claimed in claim 5 wherein the Sm content is less than or equal to 0.02% by weight.

7. The alloy as claimed in claim 1 having a magnesium content of at least 85% by weight.

8. The alloy as claimed in claim 1 wherein the alloy exhibits a corrosion rate as measured according to ASTM B117 of less than 40 Mpy.

9. The alloy as claimed in claim 1 wherein the area percentage of any precipitated particles formed during processing of the alloy having an average particle size of between 1 and 20 µm is less than 5%.

10. The alloy as claimed in claim 1 wherein when the alloy is in the T4 or T6 condition the area percentage of any precipitated particles having an average particle size of between 1 and 15 µm is less than 3%.

11. The alloy as claimed in claim 9 wherein said particles are rich in Nd, such that the particles have a percentage composition of Nd greater than the percentage composition of any other element in the particle.

12. The alloy as claimed in claim 1 when wrought.

13. The alloy as claimed in claim 2 wherein the content of Zn+Mn is up to 0.40% by weight.

14. The alloy as claimed in claim 1 wherein the content of Nd is 0.05-3.35% by weight.

15. A wrought magnesium alloy composition consisting of:
   Y in an amount of ≤0.3% by weight,
   Nd in an amount of 0.05-5% by weight,
   one or more heaving rare earths selected from Ho, Lu, Tm and Tb of above 0.5% by weight each and no more than 5.5% by weight in total,
   Zr in an amount of ≤0.1% by weight,
   Al in an amount of 1-7.5% by weight,
   one or more of Ca, Gd, Zn, Mn and
   magnesium.

16. The alloy composition of claim 15 wherein Ca is present in an amount of up to 3% by weight.

17. The alloy as claimed in claim 15 wherein Zn and/or Mn is present in an amount of up to 2% by weight in total.

18. The alloy as claimed in claim 1 wherein Al is present in an amount of up to 7.5% by weight.

19. The alloy as claimed in claim 1 wherein Dy is present in an amount of up to 8% by weight.

20. The alloy as claimed in claim 1 wherein Er is present in an amount of up to 5.5% by weight.

21. The alloy as claimed in claim 1 wherein Fe is present in an amount of up to 0.004% by weight.

22. The alloy as claimed in claim 1 wherein Si is present in an amount of up to 0.1% by weight.

23. The alloy composition of claim 15 wherein Gd is present in an amount of up to 7% by weight.

\* \* \* \* \*